(12) United States Patent
Rochat et al.

(10) Patent No.: US 8,092,608 B2
(45) Date of Patent: Jan. 10, 2012

(54) COMPOSITION COMPRISING A PREBIOTIC FOR DECREASING INFLAMMATORY PROCESS AND ABNORMAL ACTIVATION OF NON-SPECIFIC IMMUNE PARAMETERS

(75) Inventors: Florence Rochat, Montreux (CH); Eduardo Schiffrin, Crissier (CH); Yves Guigoz, Epalinges (CH)

(73) Assignee: Nestec S.A., Vevey (CH)

( * ) Notice: Subject to any disclaimer, the term of this patent is extended or adjusted under 35 U.S.C. 154(b) by 995 days.

(21) Appl. No.: 10/472,731

(22) PCT Filed: Mar. 15, 2002

(86) PCT No.: PCT/EP02/02905
§ 371 (c)(1),
(2), (4) Date: Apr. 6, 2004

(87) PCT Pub. No.: WO02/076471
PCT Pub. Date: Oct. 3, 2002

(65) Prior Publication Data
US 2004/0219157 A1    Nov. 4, 2004

(30) Foreign Application Priority Data
Mar. 22, 2001 (EP) .................................. 01201091

(51) Int. Cl.
*C08B 30/00* (2006.01)
*C13B 50/00* (2011.01)
*A01N 63/00* (2006.01)
*A01N 65/00* (2009.01)
*C12N 1/00* (2006.01)

(52) U.S. Cl. .................... 127/29; 424/93.1; 435/243
(58) Field of Classification Search .................. 127/29; 424/93.1; 435/243
See application file for complete search history.

(56) References Cited

U.S. PATENT DOCUMENTS

| 5,744,134 | A | * | 4/1998 | Paul | 424/93.4 |
| 5,849,324 | A | * | 12/1998 | Dohnalek et al. | 424/440 |
| 5,895,648 | A | * | 4/1999 | Cavaliere Vesely et al. | 424/93.4 |
| 6,130,244 | A | * | 10/2000 | DeMichele et al. | 514/474 |
| 6,203,797 | B1 | | 3/2001 | Perry | 424/639 |

FOREIGN PATENT DOCUMENTS

| WO | WO 99/07239 | 2/1999 |
| WO | WO 01/42263 A2 | 6/2001 |
| WO | WO 01/15714 A1 | 8/2001 |

OTHER PUBLICATIONS

NIDCD "Otitis Media (Ear Infection)" www.nidcd.nih.gov/health/hearing/otitism.asp Reviewed on Jul. 2002, Accessed by Examiner on Jul. 25, 2006.*
eMedicine—Chronic Granulomatous Disease : Article by Roman Nowicki, accessed http://www.emedicine.com/DERM/topic719.htm (1 of 19)Jun. 5, 2008 9:27:13 AM.*
Encyclopedia Britannica, accessed Online. Mar. 3, 2009 chronic granulomatous disease Encyclopedia Britannica http://www.britannica.com/EBchecked/topic/116133/chronic-granulomatous-disease.*
Schapiro et al. "Chronic Granulomatous Disease Presenting in a 69-year-old man" The New England Journal of Medicine, 325(25) 1786.*
Schapiro et al. "Chronic Granulomatous Disease Presenting in a 69-year-old man" The New England Journal of Medicine, (1991) 325(25) 1786.*
Ziemer et al. article entitled "An Overview of Probiotics, Prebiotics and Synbiotics in the Functional Food Concept: Perspectives and Future Strategies" *Int. Dairy Journal* 8 (1998) pp. 473-479.

* cited by examiner

*Primary Examiner* — Jon P Weber
*Assistant Examiner* — Thane Underdahl
(74) *Attorney, Agent, or Firm* — K&L Gates LLP

(57) ABSTRACT

The present invention relates to a composition comprising prebiotic (prebiotic adjuvant) for decreasing inflammatory process by improving the homeostasis of non-specific immune parameters and of lymphocyte subpopulations. It also relates to the use of a prebiotic formulation in the manufacture of a medicament or a food or petfood composition for decreasing inflammatory process and/or abnormal activation of non-specific immune parameters, such as phagocytes.

8 Claims, 3 Drawing Sheets

Figure 1:
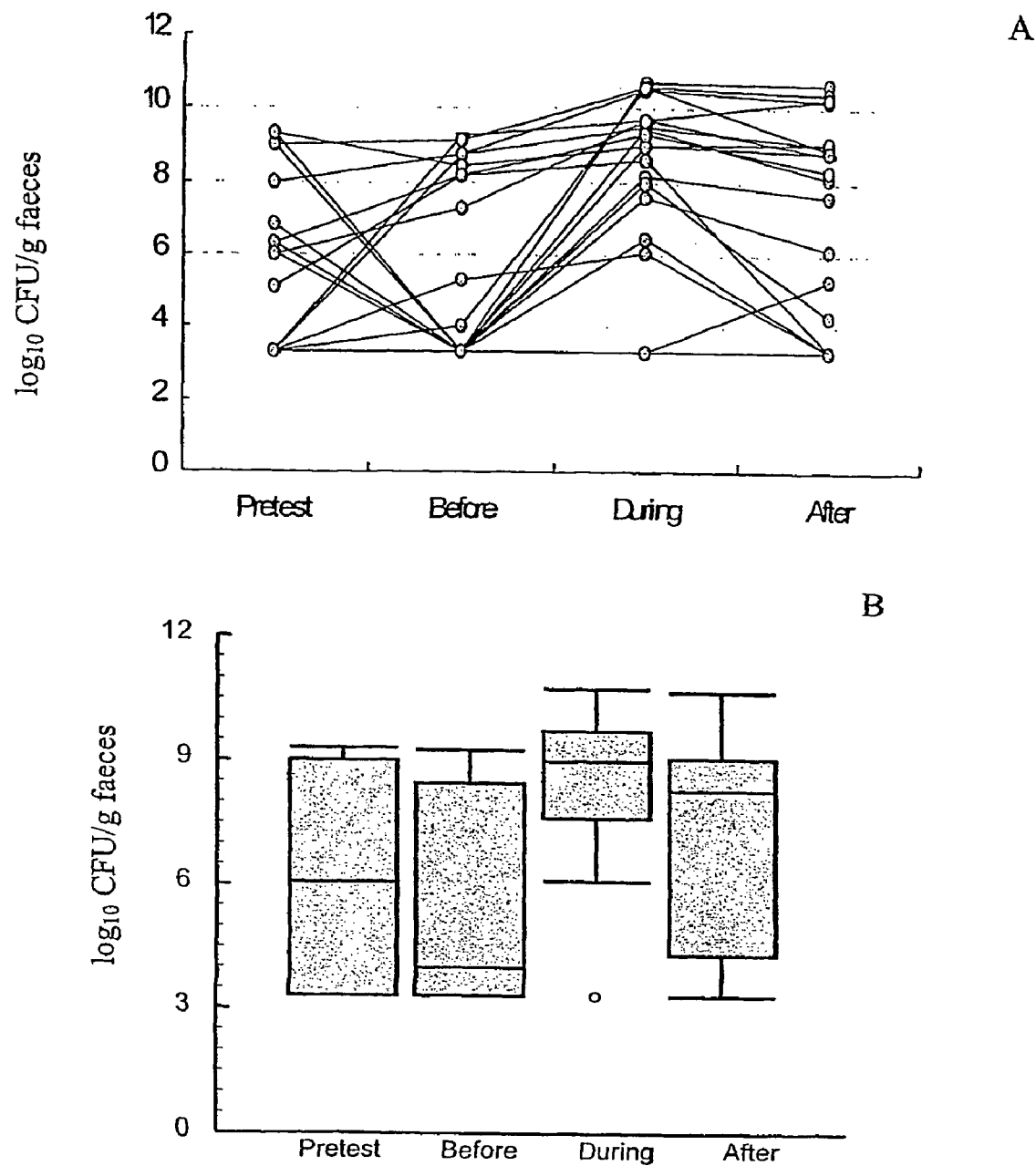

FIG. 3
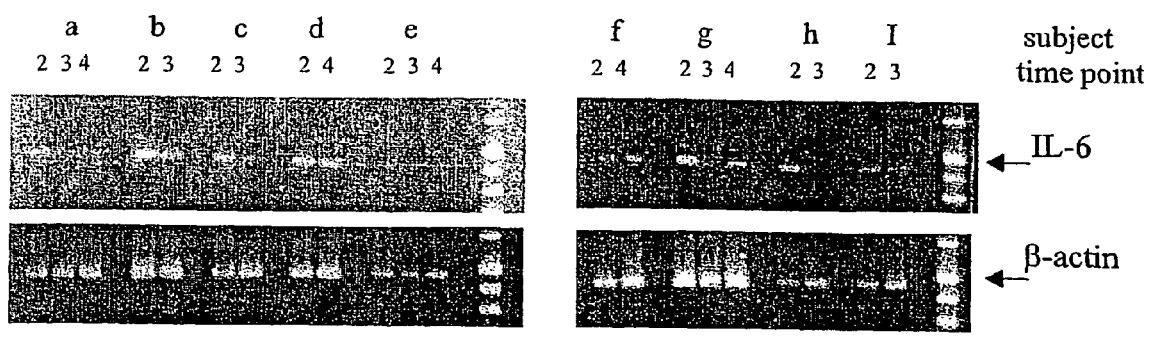
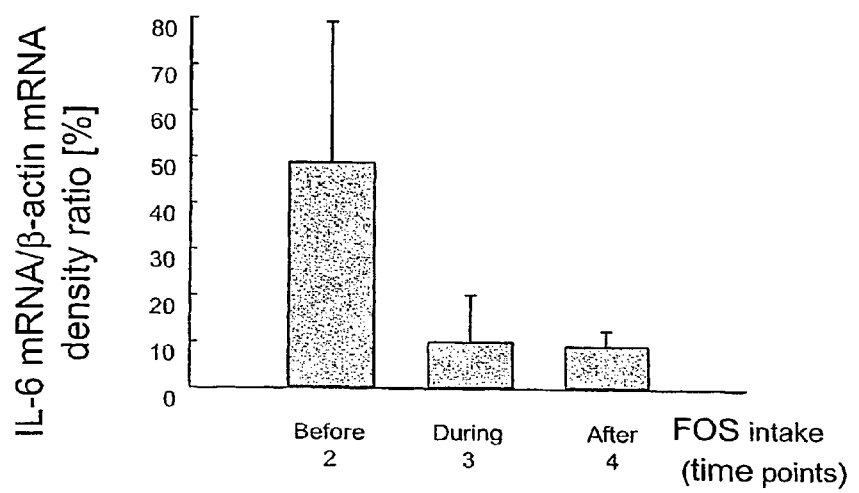

COMPOSITION COMPRISING A PREBIOTIC FOR DECREASING INFLAMMATORY PROCESS AND ABNORMAL ACTIVATION OF NON-SPECIFIC IMMUNE PARAMETERS

FIELD OF THE INVENTION

The present invention relates to a composition comprising prebiotic (prebiotic adjuvant) for decreasing inflammatory process by improving the homeostasis of non-specific immune defense parameters and of lymphocyte subpopulations. It also relates to the use of a prebiotic formulation in the manufature of a medicament or food or petfood composition for decreasing inflammatory process and/or abnormal activation of non-specific immune parameters, such as phagocytes.

BACKGROUND OF THE INVENTION

It is well known that prebiotics comprise carbohydrates and more specifically, oligosaccharides. Furthermore it is known that they have widely been used as functional food ingredients. They resist hydrolysis by enzymes of the human digestive tract, can reach the colon undegraded and provide a carbohydrate substance particulary suited to the growth of bifidobacteria Oligosaccharides may be produced from glucose, galactose, xylose, maltose, sucrose, lactose, starch, xylan, hemicellulose, inulin, gum or a mixture thereof. Purified commercially available products such as fructooligosaccharides contain greater than about 95% solids in the form of oligosaccharides.

Fructooligosaccharides have been studied in humans mainly for functional claims related to the bioavailability of minerals, lipid metabolism and and regulation of bowel habits (Roberfroid, M. B. Delzenne, N. M. *Annu Rev Nutr* 1998;18: 117-143). Little attention has been given to their effect on immunological functions, while indications for modifications of carcinogenesis and stimulation of gut-associated lymphoid tissue comes from animal studies (Pierre, F., et al. *Cancer Res* 1997;57:225-228).

Indeed, fructooligosaccharides, long (inulin) and short chain (oligofructose) are among the carbohydrates, which escape digestion in the upper gastro-intestinal tract. They are then fermented in the colon and selectively stimulate the growth of bifidobacteria.

Human intestinal flora with its important metabolic activity is possibly associated with many health related functions such as maintenance of gut homeostasis, metabolism of xenobiotics and stimulation of gut immunity. It is influenced by disease, diet, stress and possibly ageing. The large intestine contains up to $10^{12}$ bacteria/g faeces with about $10^3$ different species from approximately 40-50 genera of bacteria. Most of them are obligate anaerobes with a large population, however, of facultative anaerobes. The main anaerobe species are *Bacteroïdes*, bifidobacteria, eubacteria, which make up to 99% of the total faecal flora, followed by clostridia, lactobacilli and gram positive cocci, enterococci, coliforms, methanogens and at much lower levels sulfate-reducing bacteria (Hill, M. J. Normal gut bacterial flora. 1995;3-17).

Adult microflora characteristics are present from about 2 years of age. Adult gut microflora seems to be rather stable; although some changes have been reported with ageing, mainly low levels of bifidobacteria and *Bacteroïdes* (Hopkins, M. J., et al. *Gut* 2001;48:198-205). Gut flora can be divided into species that have beneficial effects, such as bifidobacteria, or harmful effects, such as *Pseudonioinas aeruginosa*, *Protezus* species, staphylococci, some clostridia and *Veilonellae*, and species that are intermediate in effect such as enterococci, *Escherichia coli*, Enterococci and *Bacteroïdes*. Bifidobacteria and lactobacilli have been reported to have beneficial effects on specific immune functions (Schiffrin, E. J., et al. *J Dairy Sci* 1995;78:491-497).

With age it is generally reported that bifidobacteria are diminished, while *Clostridim perfringens*, *Entercocci* and *Enterobacteriaceae* are increased (Mitsuoka, T. Hayakawa, K. *Zentralbl Bakteriol [Orig A]* 1973;223:333-342). Bacterial overgrowth occurs more frequently in the elderly due to the high prevalence of atrophic gastritis and hypochlorhydria. Bacterial overgrowth seems to be free of clinical symptoms in healthy elderly, it may have some importance in frail elderly $\geq 75$ year of age, and *Clostridium difficile* associated diarrhea is more frequent in the elderly in acute care or long-term care, in association with antibiotic treatment and possibly decreased immune response. Ageing is related with a loss in immune function and the existence of an interrelationship between nutrition and immune function has been recognized (Meydani, S. N. Status of Nutritional Immunology Studies: *J Nutr Immunol* 1994;2:93-97).

Changes in immune response (remodeling of cytokine production and dysregulation of the immune functions) is associated with increased incidence of infections and mortality linked to infection. Nutritional interventions, mainly vitamin and mineral supplementation, can improve the immune response in frail elderly [Lesourd, B. M. Am *J Clin Nutr* 1997;66:478S-484S41].

The present invention aims to provide another composition able to limit the dysregulation of the immune function, and more particularly the abnormal activation of non-specific immune response such as the phagocytes and the monocyte macrophage cell system as well as preserve lymphocyte subpopulations in normal level of activation.

SUMMARY OF THE INVENTION

Consequently, in a first aspect the present invention provides a composition comprising at least one prebiotic for decreasing inflammatory process and/or abnormal activation of non-specific immune parameters.

It may be particularly intended for decreasing abnormal activation of phagocytes, for example.

It has been surprisingly found that a prebiotic supplementation can induce decrease in inflammatory process, and particularly can induce changes in non-specific immunity, such as decreased phagocytic activity, as well as a decreased expression of interleukin-6 mRNA in peripheral blood monocytes.

In a second aspect the invention provides the use of at least one prebiotic in the manufature of a medicament or a food or pet food composition for decreasing inflammatory process in a mammal.

In a third aspect the invention provides use of at least one prebiotic in the manufature of a medicament or a food or pet food composition for decreasing abnormal activation of non-specific immune parameters in a mammal.

In a forth aspect the invention provides a method of decreasing inflammatory process in a mammal, which comprises administering an effective amount of a prebiotic or composition comprising at least one prebiotic.

In a fifth aspect the invention provides a method of decreasing abnormal activation of non-specific immune parameters in a mammal, which comprises administering an effective amount of a prebiotic or composition comprising at least one prebiotic.

An advantage of the present invention is that it provides a decrease in inflammatory process, particularly a decrease expression of Interleukine-6 mRNA in peripheral blood mononuclear cells.

Another advantage of the present invention is that it provides a decrease in phagocytic activity of granulocytes and monocytes, particularly in frail patient with chronic inflammatory situation.

Yet another advantage of the present invention is that it may be used to improve the inflammatory situation in a mammal and thus reduce the risk of development of deleterious infections, by simple consumption of a food composition according to the present invention. It will be appreciated that intravenous or subcutaneous administration of a drug requires expertise, and compared to oral administration it is not as safe, convenient or acceptable to the patient. In the light of these concerns, the invention provides the clear advantage of a nutritional and/or therapeutic product which may be administered orally.

DETAILED DESCRIPTION

According to a first aspect, the composition preferably comprises at least one prebiotic or a prebiotic mixture.

Preferably, the prebiotic comprises an oligosachharide produced from glucose, galactose, xylose, maltose, sucrose, lactose, starch, xylan, hemicellulose, inulin, gum (acacia gum, for example) or a mixture thereof. More preferably the oligosaccharide comprises fructooligosaccharide (FOS). Most preferably the prebiotic comprises a mixture of fructooligosaccharide and inulin. Preferably this mixture comprises PREBIO1® or a mixture of commercially available RAFTILOSE® and RAFTILINE®.

Preferably, the prebiotic comprises about 50% to about 95% FOS. More preferably it comprises about 60% to about 80% FOS. Most preferably it comprises about 70% FOS.

Preferably, the prebiotic comprises about 10% to about 50% inulin. More preferably it comprises about 20% to about 40% inulin. Most preferably it comprises about 30% inulin.

The prebiotic may comprise a mixture of fructooligosaccharides and inulin in the amounts by weight of 70% fructooligosaccharides and 30% inulin.

Preferably, the composition comprises a probiotic in addition to the prebiotic. The probiotic may be *Bifidobacterium bifidum* or *Streptococcus thermophilus*, for example. Preferably the *Bifidobacterium bifidum* is *Bifidobacterium lactis*.

In one embodiment, the composition may be a complete and nutritionally balanced food or pet food. It can also be a dietary supplement, for example. It is preferably adressed to elderly human or elderly pet, or critically ill patients with chronic inflammation.

Accordingly, a nutritionally complete pet food can be prepared. The nutritionally complete pet food may be in any suitable form; for example in dried form, semi-moist form or wet form; it may be a chilled or shelf stable pet food product. These pet foods may be produced as is conventional. Preferably, the prebiotic is provided in the form of plant material, which contains the prebiotic. Suitable plant materials include asparagus, artichokes, onions, wheat, yacon or chicory, or residues of these plant materials. Alternatively, the prebiotic may be provided as an inulin extract or its hydrolysis products commonly known as fructooligosaccharides, galacto-oligosaccharides, xylo-oligosaccharides or oligo derivatives of starch. Extracts from chicory are particularly suitable. The maximum level of prebiotic in the pet food is preferably about 20% by weight; especially about 10% by weight. For example, the prebiotic may comprise about 0.1% to about 5% by weight of the pet food. For pet foods which use chicory as the prebiotic, the chicory may be included to comprise about 0.5% to about 10% by weight of the feed mixture; more preferably about 1% to about 5% by weight.

Apart from the prebiotic according to the invention, these pet foods may include any one or more of a carbohydrate source, a protein source and lipid source.

Any suitable carbohydrate source may be used. Preferably the carbohydrate source is provided in the form of grains, flours and starches. For example, the carbohydrate source may be rice, barley, sorghum, millet, oat, corn meal or wheat flour. Simple sugars such as sucrose, glucose and corn syrups may also be used. The amount of carbohydrate provided by the carbohydrate source may be selected as desired. For example, the pet food may contain up to about 60% by weight of carbohydrate.

Suitable protein sources may be selected from any suitable animal or vegetable protein source; for example muscular or skeletal meat, meat and bone meal, poultry meal, fish meal, milk proteins, corn gluten, wheat gluten, soy flour, soy protein concentrates, soy protein isolates, egg proteins, whey, casein, gluten, and the like. For elderly animals, it is preferred for the protein source to contain a high quality animal protein. The amount of protein provided by the protein source may be selected as desired. For example, the pet food may contain about 12% to about 70% by weight of protein on a dry basis.

The pet food may contain a fat source. Any suitable fat source may be used both animal fats and vegetable fats. Preferably the fat source is an animal fat source such as tallow. Vegetable oils such as corn oil, sunflower oil, safflower oil, rape seed oil, soy bean oil, olive oil and other oils rich in monounsaturated and polyunsaturated fatty acids, may also be used. In addition to essential fatty acids (linoleic and alpha-linoleic acid) the fat source may include long chain fatty acids. Suitable long chain fatty acids include, gamma linoleic acid, stearidonic acid, arachidonic acid, eicosapentanoic acid, and docosahexanoic acid. Fish oils are a suitable source of eicosapentanoic acids and docosahexanoic acid. Borage oil, blackcurrent seed oil and evening primrose oil are suitable sources of gamma linoleic acid. Rapeseed oil, soybean oil, linseed oil and walnut oil are suitable sources of alpha-linoleic acid. Safflower oils, sunflower oils, corn oils and soybean oils are suitable sources of linoleic acid. Olive oil, rapeseed oil (canola) high oleic sunflower and safflower, peanut oil, rice bran oil are suitable sources of monounsaturated fatty acids. The amount of fat provided by the fat source may be selected as desired. For example, the pet food may contain about 5% to about 40% by weight of fat on a dry basis. Preferably, the pet food has a relatively reduced amount of fat.

The pet food may contain other active agents such as long chain fatty acids. Suitable long chain fatty acids include alpha-linoleic acid, gamma linoleic acid, linoleic acid, eicosapentanoic acid, and docosahexanoic acid. Fish oils are a suitable source of eicosapentanoic acids and docosahexanoic acid. Borage oil, blackcurrent seed oil and evening primrose oil are suitable sources of gamma linoleic acid. Safflower oils, sunflower oils, corn oils and soybean oils are suitable sources of linoleic acid.

The choice of the carbohydrate, protein and lipid sources is not critical and will be selected based upon nutritional needs of the animal, palatability considerations, and the type of product produced. Further, various other ingredients, for example, sugar, salt, spices, seasonings, vitamins, minerals, flavoring agents, gums, and probiotic micro-organisms may also be incorporated into the pet food as desired A probiotic microorganism may also be added. It may be selected from one or more microorganisms suitable for animal consumption and which is able to improve the microbial balance in the intestine. Examples of suitable probiotic micro-organisms include yeast such as *Saccharomyces*, *Debaromyces*, *Candida*, *Pichia* and *Torulopsis*, moulds such as *Aspergillus*, *Rhizopus*, *Mucor*, and *Penicillim* and *Torulopsis* and bacteria such as the genera *Bifidobacterium*, *Bacteroides*, *Clostridium*, *Fusobacterium*, *Melissococcus*, *Propionibacterium*, *Streptococcus*, *Enterococcus*, *Lactococcus*, *Staphylococcus*, *Peptostrepococcus*, *Bacillus*, *Pediococcus*, *Micrococcus*, *Leuconostoc*, *Weissella*, *Aerococcus*, *Oenococcus* and *Lactobacillus*. The probiotic micro-organisms may be in powdered, dried form; especially in spore form for micro-organisms which form spores. Further, if desired, the probiotic micro-organism may be encapsulated to further increase the probability of survival; for example in a sugar matrix, fat matrix or polysaccharide matrix. If a probiotic micro-organism is used, the pet food preferably contains about $10^4$ to about $10^{10}$ cells of the probiotic micro-organism per gram of the pet food; more preferably about $10^6$ to about $10^8$ cells of the probiotic micro-organism per gram. The pet food may contain about 0.5% to about 20% by weight of the mixture of the probiotic micro-organism; preferably about 1% to about 6% by weight; for example about 3% to about 6% by weight.

For elderly pets, the pet food preferably contains proportionally less fat than pet foods for younger pets. Further, the starch sources may include one or more of oat, rice, barley, wheat and corn.

For dried pet foods a suitable process is extension cooking, although baking and other suitable processes may be used. When extrusion cooked, the dried pet food is usually provided in the form of a kibble. If a prebiotic is used, the prebiotic may be admixed with the other ingredients of the dried pet food prior to processing. A suitable process is described in European patent application No 0850569;. If a probiotic micro-organism is used, the organism is best coated onto or filled into the dried pet food. A suitable process is described in European patent application No 0862863.

For wet pet foods, the processes described in U.S. Pat. Nos. 4,781,939 and 5,132,137 may be used to produce simulated meat products. Other procedures for producing chunk type products may also be used; for example cooking in a steam oven. Alternatively, loaf type products may be produced by emulsifying a suitable meat material to produce a meat emulsion, adding a suitable gelling agent, and heating the meat emulsion prior to filling into cans or other containers.

In another embodiment, a food composition for human consumption is prepared. This composition may be a nutritional complete formula, a dairy product, a chilled or shelf stable beverage, soup, a dietary supplement, a meal replacement, and a nutritional bar or a confectionery.

Apart from the prebiotic according to the invention, the nutritional formula may comprise a source of protein. Dietary proteins are preferably used as a source of protein. The dietary proteins may be any suitable dietary protein; for example animal proteins (such as milk proteins, meat proteins and egg proteins); vegetable proteins (such as soy protein, wheat protein, rice protein, and pea protein); mixtures of free amino acids; or combinations thereof. Milk proteins such as casein, whey proteins and soy proteins are particularly preferred. The composition may also contain a source of carbohydrates and a source of fat.

If the nutritional formula includes a fat source, the fat source preferably provides about 5% to about 55% of the energy of the nutritional formula; for example about 20% to about 50% of the energy. The lipids making up the fat source may be any suitable fat or fat mixtures. Vegetable fats are particularly suitable; for example soy oil, palm oil, coconut oil, safflower oil, sunflower oil, corn oil, canola oil, lecithins, and the like. Animal fats such as milk fats may also be added if desired.

A source of carbohydrate may be added to the nutritional formula. It preferably provides about 40% to about 80% of the energy of the nutritional composition. Any suitable carbohydrates may be used, for example sucrose, lactose, glucose, fructose, corn syrup solids, and maltodextrins, and mixtures thereof. Dietary fibre may also be added if desired. If used, it preferably comprises up to about 5% of the energy of the nutritional formula. The dietary fibre may be from any suitable origin, including for example soy, pea, oat, pectin, guar gum, gum arabic, and fructooligosaccharides. Suitable vitamins and minerals may be included in the nutritional formula in an amount to meet the appropriate guidelines.

One or more food grade emulsifiers may be incorporated into the nutritional formula if desired; for example diacetyl tartaric acid esters of mono- and di-glycerides, lecithin and mono- and di-glycerides. Similarly suitable salts and stabilisers may be included.

The nutritional formula is preferably enterally administrable; for example in the form of a powder, tablet, capsule, a liquid concentrate, solid product or a ready-to-drink beverage. If it is desired to produce a powdered nutritional formula, the homogenised mixture is transferred to a suitable drying apparatus such as a spray drier or freeze drier and converted to powder.

In another embodiment, a nutritional composition comprises a milk based cereal together with a prebiotic formulation. Preferably the milk based cereal is an infant cereal which acts as a carrier for the prebiotic formulation.

In another embodiment, a usual food product may be enriched with at least one prebiotic according to the present invention. For example, a fermented milk, a yoghurt, a fresh cheese, a renneted milk, article of confectionery, for example a sweet or sweetened beverage, a confectionery bar, breakfast cereal flakes or bars, drinks, milk powders, soy-based products, non-milk fermented products or nutritional supplements for clinical nutrition. Then, the amount of the composition added is preferably at least about 0.01% by weight.

The following examples are given by way of illustration only and in no way should be construed as limiting the subject matter of the present application. Percentages and parts are by weight unless otherwise indicated. The example are preceeded by a brief description of the figures.

FIG. 1: Effect of feeding 8 g of short-chain fructooligosaccharides (FOS) on viable counts of bifidobacteria in fresh faecal samples of nursing home elderly. Time points were before (2), during (3), and after (4) period of 3 weeks of FOS intake. (A) Individual values. (B) Box plots. Boxes indicate $25^{th}$ and $75^{th}$ percentiles, solid lines inside box indicate median values, and t-shapes $5^{th}$ and $95^{th}$ percentiles; solid dot indicates outlying value.

Figure 2:
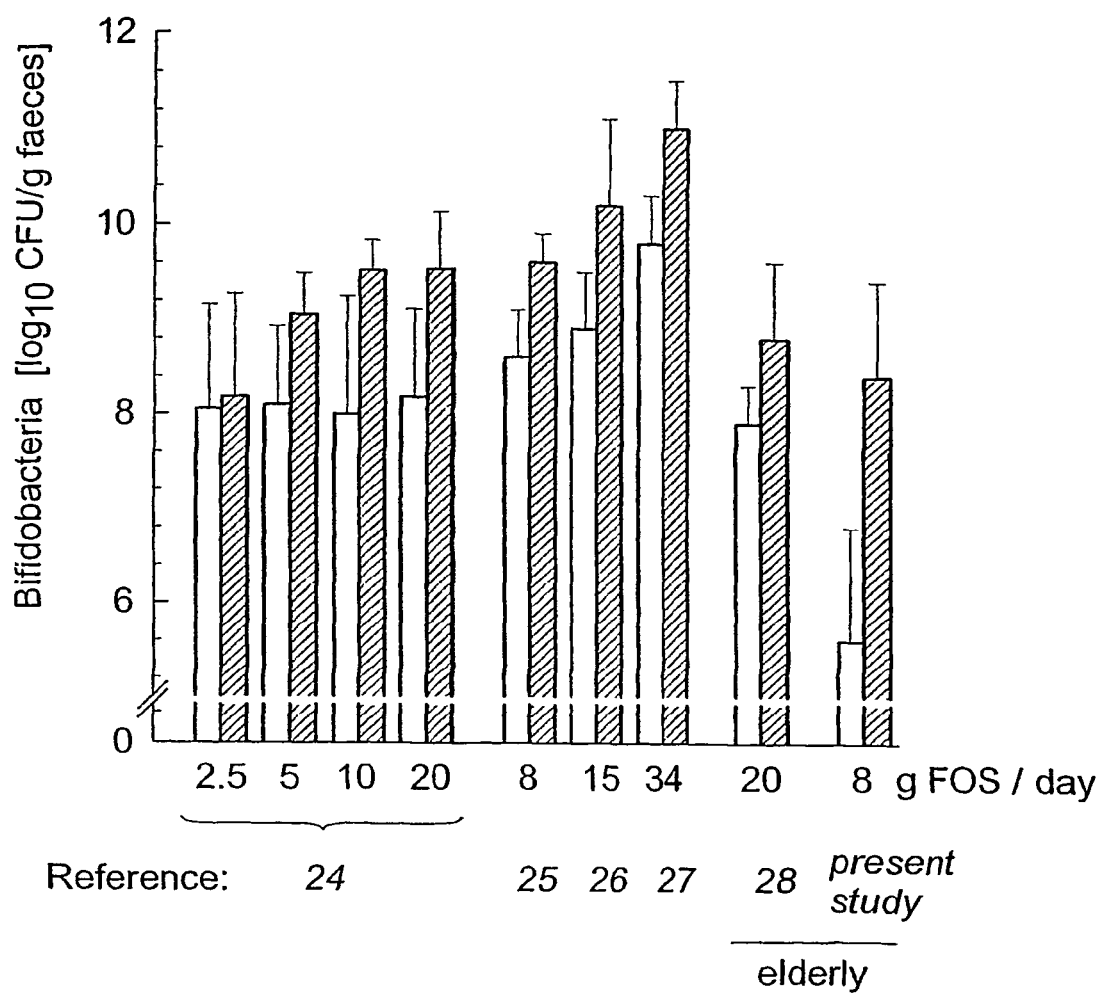

FIG. 2: Effect of fructooligosaccharides (FOS) on bifidobacteria in adults and elderly. Reference 24 (Bouhnik Y et al. J Nutr 1999; 129:113) dose response from 2.5 to 20 g FOS/day in 18-47 year old adults; Reference 25 (Menne E et al. J Nutr 2000;130:1197) response to 8 g FOS/day in 20-50 year old adults; Reference 26 (Gibson G R J Nutr 1999;129:1438S) response to 15 gFOS/day in young adults; Reference 27 (Kruse H P et al. Brit J Nutr 1999;82:375) response to inulin up to 34 g/day in 26-53 year old adults; Reference 28 (Kleessen B et al. Am J Clin Nutr 1997; 65:1397) response to 20 g FOS/day in elderly constipated subjects aged 68-89 years; Present study: resposne to 8 g FOS/day in nursing home subjects aged 77-91 years.

FIG. 3: Differences in IL-6 mRNA expression in peripheral blood mononuclear cells (PBMC) of elderly supplemented with FOS. IL-6 mRNA expression in PBMC was measured by reverse transcription-polymerase chain reaction (RT-PCR). Estimation of quantitative changes were done by scanning band intensity using NIH-image program and calculated as density ratio of IL-6 mRNA to β-actin mRNA in percent. Time points were before (2), during (3), and after (4) period of 3 weeks of FOS intake. (A) Representative image of individual changes from ethidium bromide stained gels. (B) Quantitative estimation of IL-6 mRNA expression: Changes in IL6-mRNA during FOS intakes are significantly different from before FOS intakes (p=0.018).

Example 1

Effects of Oligosaccharide on the Faecal Flora And Non-Specific Immune System in Elderly People Materials and Methods
Study Design The study was a pretest/posttest study of 19 elderly nursing home patients (see study scheme).

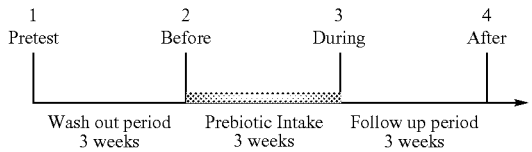

Measure of body weight and sample collection for stool, blood and urine were at time point 1 (pretest or at the beginning of the wash out period), 2 (before prebiotic intake), 3 (during prebiotic intake) and 4 (after follow up period)

During the whole study, intake of fermented dairy products were restricted and fructooligosaccharides containing food (onion, leek, chicory roots) were limited.

Subjects

Nineteen elderly subjects in a nursing home were recruited for the study. Subjects fulfilling one or more of the following criteria were excluded from participation in the study:
    Antibiotic treatment in the past month
    Chronic intestinal disorder
    Particular dietary regimen (i.e. vegetarian)
    Diagnosis of gastrointestinal cancer
    Presence of flatulence Approval was obtained from the institutional ethical committee. Written informed consent was obtained from all subjects. The study was carried out at a local nursing home, Le Mont-Pèlerin, Switzerland.

Nutritional Status

At entrance into study nutritional status was evaluated by the Mini Nutritional Assessemnt (MNA) test which includes the following items: anthropometric measurements (calf and arm circumference, height, weight and weight loss), general assessments (lifestyle, medications, mobility), dietary questionnaires (number of meals, fluid and food intakes, autonomy of feeding) and subjective assessments (self perception for health and nutrition.) [Guigoz, Y., et al. Nutr Rev 1996;54:S59-565]. MNA classified the elderly nutritional status using a 30 point scale: MNA≧24=wellnourished, MNA 17-23.5=at risk of malnutrition and MNA<17=malnourished.

Prebiotic Supplementation

Eight gram of short chain fructooligosaccharides (FOS) per day was administered as follows: twice a day 4 g FOS powder (Actilight 950P, Bëghin-Meiji industries, Neuilly-sur-Seine, France) were incorporated in a dish at the time of the meal by the nurses. For estimation of compliance, the daily consumption of the supplement was recorded by the nurses on a daily record sheet.

Microbial Investigations

The endogenous populations of Lactobacilli, Bacteroïdes, Enterobacteriaceae, Enterococci, Bifidobacteria and Clostridium peifringens were counted.

Stool samples were collected at day 0, 21, 42 and 63 from each subject. The stool samples were immediately (within 30 minutes) placed in an anaerobic jar and kept at 4° C. until analysis (a maximum of 6 hours). Hundred fold serial dilutions were performed in pre-reduced Ringer solution containing 0.5% of cystein, from −2 to −8. Petri dishes of various media were inoculated and incubated for 48 hr at 37° C. in anaerobic atmosphere using Anaerocult A (Merck, Darmstadt, Germany), except for Enterococci and Enterobacteriacea incubated for 24 hr at 37° C. in aerobic atmosphere. Bacteria were detected on selective or half-selective media as follows: Enterobacteriacea on Drigalski medium (Sanofi Diagnostics Pasteur, France), Bifidobacteria on Eugon Tomato medium (Wadsworth Anaerobic Bacteriology Manual, V. Suter, D. Citron and S. Finegold Third edition), Lactobacilli in MRS (Difco, MI. USA) with antibiotics (Phosphomycine (79.5 mg/l)+Sulfamethoxazole (0.93 mg/l)+Trimethoprime (5 mg/l)), Clostridium perfringens on NN agar (Lowbury and Lilly, 1995), Bacteroïdes on Schaedler Neo-Vanco medium (BioMérieux, Marcy-l'Etoile, France), and Enterococci on Azide agar (Difco).

After incubation, the colonies were counted and further identified if necessary. Lactobacilli and Bifidobacteria strains were identified by microscopy, and biochemically using the API gallery system (BioMérieux), API 50 CHL gallery for lactobacilli, and API ID 32A gallery for Bifidobacteria respectively. Bacterial counts are expressed as $\log_{10}$ colony-forming units (CFUs) per gram of fresh faecal sample, with a detection limit at 3.30 cfu/g.

Faecal PH

Faecal pH was measured just after emission by the nurse at three different points in crude faeces with a microelectrode (Orion). The mean pH was calculated for each time point.

Blood Sampling

Fasting blood samples were drawn before the start of the study (4 ml) and at day 0, 21, 42 and 63 (23 ml) from each subject. Blood was taken in the morning (before 10 a.m.) after an overnight fast. Samples collected in vacutainer tubes. 13 ml were collected in heparinized tube, and 10 ml were allowed to clot at room temperature for 30-60 minutes. Serum samples were kept frozen at −70° C. until analysis. Heparinized blood was used for the functional immune parameters (phagocytosis, see below) and hematology.

Immunological Analysis

Populations of peripheral blood mononuclear cells and their phagocytic activity were analyzed in fresh samples of heparinized blood using Simulset and Pagotest (Becton Dickinson, Basel, Switzerland).

Analysis of interleukin-6 mRNA expression by PCR: Analysis of mRNA expression in the peripheral blood mononuclear cells was evaluated by PCR according to the method described by Delneste, Y., et al. (*Nutr Rev* 1998; 56:S93-S98). Primer sequences were:

(SEQ ID NO: 1)
5'-CTGCAGGAACTGGATCAGGACTTTTGTACT-3'
and (SEQ ID NO: 2)
5'-GCCTTCGGTCCAGTTGCCTTCTCCCTGGGG-3'
for interleukin-6 (IL-6) and (SEQ ID NO: 3)
5'CGTTTCCCGCTCGGCCGTGGTGGTGAAGC-3'
and (SEQ ID NO: 4)
5'-GGCGACGAGGCCCAGAGCAAGAGAGGCATC-3'
for β-actin.

Biochemical Measurements

Serum albumin, transthyretin (prealbumin), C-reactive protein, and a, acid glycoprotein concentrations were analyzed by immuno-nephelometry with a Behring Nephelometer (methods and reagents from Behring, Marburg, Germany). Serum folate and vitamin $B_{12}$ (cobalamin) concentrations were analyzed by radioimmunoassay (Dual Count, Diagnostic Product Corporation, Los Angeles, Calif., USA).

Statistical Analysis

One sample t-test or Wilcoxon signed-rank test were computed on the mean differences to evaluate the statistical significance at 0.05% level for the main hypothesis: Is there an effect of prebiotics on the different parameters measured? Further one sample t-test were computed on the mean differences to evaluate the statistical significance at 0.025% level (correction for the loss of degree of freedom) for the two question related to the design of the study, which included pre and post test periods: Is there an effect of stopping fermented milk (=wash-out period) on the different parameters measured? Is there an effect of stopping prebiotics (=follow-up period) on the different parameters measured? All statistical analysis were done using the NCSS 6.0.22 statistical software.

Results

Subjects

The 19 subjects, 4 men and 15 women, had a mean age of 85±6.0 years (77-97 year old). Women were significantly lighter than men. Subjects' characteristics at start of study are given in table 1.

TABLE 1

Subjects characteristics

| | | mean | 95% confidence interval | Range min | Max |
|---|---|---|---|---|---|
| Men n = 4 | | | | | |
| Age | [year] | 84 | 5.7 | 77 | 91 |
| Body weight | [kg] | 72.1 | 13.8 | 60.4 | 92.4 |
| BMI | [kg/mE2] | 27.5 | 5.5 | 23.4 | 35.7 |
| MNA score | [pts] | 27.0 | 2.9 | 24.0 | 30.0 |
| Albumin | [g/L] | 36.3 | 1.7 | 31.1 | 40.9 |
| Transthyretin | [g/L] | 0.23 | 0.04 | 0.17 | 0.28 |
| α1-acid glycoprotein | [g/L] | 0.98 | 0.16 | 0.82 | 1.20 |
| C-reactive protein | [mg/L] | 15 | 12 | 3 | 28 |
| Cholesterol | [mmol/l] | 4.23 | 1.26 | 2.92 | 6.00 |
| Triglycerides | [mmol/l] | 1.39 | 0.59 | 0.65 | 1.99 |
| Phospholipids | [mmol/l] | 2.10 | 0.51 | 1.52 | 2.78 |
| Women n = 15 | | | | | |
| Age | [year] | 85 | 3.1 | 77 | 97 |
| Body weight | [kg] | 57.5 | 5.8 | 39.7 | 80.0 |
| BMI | [kg/mE2] | 25.7 | 1.7 | 17.5 | 30.7 |
| MNA score | [pts] | 23.9 | 1.4 | 17.0 | 28.0 |
| Albumin | [g/L] | 36.8 | 1.7 | 31.1 | 42.7 |
| Transthyretin | [g/L] | 0.22 | 0.02 | 0.15 | 0.23 |
| α1-acid glycoprotein | [g/L] | 0.85 | 0.10 | 0.56 | 1.19 |
| C-reactive protein | [mg/L] | 5 | 2 | 1 | 15 |
| Cholesterol | [mmol/l] | 5.72 | 0.56 | 3.81 | 7.69 |
| Triglycerides | [mmol/l] | 1.51 | 0.23 | 1.11 | 2.55 |
| Phospholipids | [mmol/l] | 2.55 | 0.18 | 2.03 | 3.21 |

Only one subject was malnourished, the 7 women at risk of malnutrition were in the upper-score range 21.5-23, and the mean MNA score was in the wellnourished range: 24.6±3.0 points.

Serum albumin (normal range 35-55 g/L) and transthyretin (prealbumin; normal range 0.16-0.40) were in the lower normal range, while the acute phase proteins, α1-acid glycoprotein (normal range 0.5-1.3) and C-reactive protein (normal values <10 mg/L and abnormal values for elderly >20 mg/L) indicated no presence of inflammatory process, except for 2 men (elevated C-reactive protein levels) and 2 women (low albumin levels with normal transthyretin and borderline C-reactive protein). These results suggest a group of elderly who were still wellnourished but rather frail.

Bacteriological Analyses and Faecal PH

Bacterial counts of bifidobacteria were increased by a mean of 2.8±0.57 $\log_{10}$CFU during the 3 weeks of FOS supplementation (p<0.001), but *Bacteroïdes counts were also increased p<0.032* (see tables 2a & 2b and FIG. 1).

TABLE 2a

Effect of FOS administration on faecal flora and pH

| | Pretest | | Before | | During | | After | |
|---|---|---|---|---|---|---|---|---|
| | administration of fructooligosaccharides (8 g/day) | | | | | | | |
| Faecal variable | mean | 95% CI | mean | 95% CI | mean | 95% CI | mean | 95% CI |
| | $\log_{10}$CFU/g faeces | | | | | | | |
| *Enterobacteriaceae* | 7.7 | 0.6 | 7.2 | 0.8 | 7.1 | 0.9 | 8.0 | 0.7 |
| *Enterococci* | 6.1 | 0.8 | 5.7 | 0.9 | 5.4 | 0.8 | 6.2 | 0.9 |
| *Bifidobacteria* | 6.0 | 1.1 | 5.6 | 1.2 | 8.4 | 1.0 | 7.3 | 1.2 |
| *Lactobacilli* | 5.1 | 0.6 | 5.1 | 0.6 | 5.7 | 1.0 | 5.1 | 0.7 |
| *Bacteroïdes* | 8.8 | 0.3 | 8.6 | 0.3 | 9.3 | 0.3 | 9.8 | 0.3 |

TABLE 2a-continued

Effect of FOS administration on faecal flora and pH

| Faecal variable | Pretest mean | 95% CI | Before mean | 95% CI | During mean | 95% CI | After mean | 95% CI |
|---|---|---|---|---|---|---|---|---|
| | administration of fructooligosaccharides (8 g/day) | | | | | | | |
| | | | | | $\log_{10}$CFU/g faeces | | | |
| *Clostridium perfringens* | 3.5 | 0.2 | 3.7 | 0.5 | 3.7 | 0.5 | 3.5 | 0.4 |
| | | | | | pH | | | |
| pH | 7.1 | 0.2 | 6.9 | 0.2 | 7.0 | 0.2 | 7.0 | 0.2 |

95% CI = ±95% confidence interval

Bacterial counts for *Enterobacteriaceae*, Enterococci, and lactobacilli were not significantly affected by suppression of fermented milk products and/or the ingestion of fructooligosaccharides (FOS). While for bifidobacteria the effect seems to be a specific response to the ingestion of FOS, it resulted mainly in increased counts of bifidobacteria for subjects showing a $\log_{10}$ CFU lower than 7 before starting FOS. Suppression of FOS supplementation significantly decreased counts of bifidobacteria by 1.1±0.39 $\log_{10}$ CFU, but not to start level (tables 2a & 2b and FIG. 1). In FIG. 2 changes in bifidobacteria obtained in this study are compared to previous studies indicating that elderly are at least as sensitive to the effect of FOS as younger adults. Neither the suppression of fermented milk products nor the ingestion of FOS changed faecal pH (table 2a).

Non-Specific Immunity

Ingestion of FOS resulted in a significant increased percentage of peripheral T lymphocytes as well as the lymphocyte subsets, CD4+, CD8+ T cells (tables 3a & 3b). Total number of white blood cells, activated T lymphocytes and natural killer (NK) cells were not affected by the ingestion of FOS (tables 3a & 3b).

TABLE 3a

Peripheral immunological parameters: lymphocyte subpopulations

| Variable | Units | Pretest Mean | 95% CI | Before Mean | 95% CI | During Mean | 95% CI | After Mean | 95% CI |
|---|---|---|---|---|---|---|---|---|---|
| | | | | Administration of fructooligosaccharides (8 g/day) | | | | | |
| White blood cells | # $10^{-3}$ | nd | | 4.9 | 0.6 | 5.3 | 0.7 | 5.8 | 0.7 |
| T lymphocytes | % | 65.7 | 4.8 | 64.0 | 4.3 | 68.7 | 5.4 | 66.9 | 4.1 |
| B lymphocytes | % | 7.7 | 1.5 | 8.3 | 1.7 | 8.5 | 1.4 | 8.1 | 1.5 |
| CD 4$^+$ cells | % | 40.8 | 4.4 | 41.7 | 4.1 | 47.3 | 4.5 | 45.1 | 4.0 |
| CD 8$^+$ cells | % | 35.3 | 4.4 | 33.2 | 4.5 | 38.3 | 4.7 | 36.8 | 4.7 |
| Activated T lymphocytes | % | 15.0 | 3.8 | 15.7 | 4.1 | 15.6 | 4.7 | 18.6 | 5.3 |
| NK cells | % | 22.0 | 3.9 | 21.9 | 3.4 | 24.8 | 3.4 | 21.3 | 3.3 |

95% CI = ±95% confidence interval

TABLE 3b-c-d

Changes in peripheral immunological parameters
Data given are the mean difference ± standard error
of the mean (sem) after each period of 3 weeks

| | | No fermented milk Products (Wash-out period) | | |
|---|---|---|---|---|
| n = 13-19 | units | Mean $\Delta^2$ | ±sem | p value[5] |
| White blood cells | # $10^{-3}$ | — | — | — |
| T lymphocytes | % | −1.7 | 0.97 | 0.157 |
| B lymphocytes | % | 0.4 | 0.34 | 0.298 |
| CD 4$^+$ cells | % | 0.8 | 0.91 | 0.397 |
| CD 8$^+$ cells | % | −2.1 | 0.82 | 0.019 |
| Activated T lymphocytes | % | 0.7 | 0.72 | 0.353 |
| NK cells | % | 0.05 | 1.15 | 0.964 |
| | | FOS[1] 8 g/day (Prebiotic intake period) | | |
| n = 13-19 | units | Mean $\Delta^3$ | ±sem | p value[5] |
| White blood cells | # $10^{-3}$ | 0.347 | 0.286 | 0.243 |
| T lymphocytes | % | 4.6 | 1.49 | 0.006 |
| B lymphocytes | % | 0.3 | 0.44 | 0.562 |
| CD 4$^+$ cells | % | 5.7 | 1.34 | <0.001 |

TABLE 3b-c-d-continued

Changes in peripheral immunological parameters
Data given are the mean difference ± standard error
of the mean (sem) after each period of 3 weeks

| | | | | |
|---|---|---|---|---|
| CD 8+ cells | % | 5.0 | 0.99 | <0.001 |
| Activated T lymphocytes | % | −0.1 | 1.00 | 0.918 |
| NK cells | % | 2.9 | 1.48 | 0.066 |

| | | No FOS (Follow-up period) | | |
|---|---|---|---|---|
| n = 13-19 | units | Mean Δ[4] | ±sem | p value[5] |
| White blood cells | #$10^{-3}$ | 0.495 | 0.362 | 0.326 |
| T lymphocytes | % | −1.8 | 1.42 | 0.225 |
| B lymphocytes | % | −0.4 | 0.46 | 0.434 |
| CD 4+ cells | % | −2.3 | 1.38 | 0.111 |
| CD 8+ cells | % | −1.4 | 1.14 | 0.227 |
| Activated T lymphocytes | % | 3.0 | 0.93 | 0.005 |
| NK cells | % | −3.6 | 1.40 | 0.020 |

[1]FOS = 4 g/twice a day,
[2]Effect of stopping fermented milk products = Mean change between the pretest sampling and the start of the prebiotic supplementation (3 weeks wash-out period),
[3]Effect of FOS supplementation (4 g/twice a day) = Mean change between the start of the prebiotic supplementation and the end of supplementation (3 weeks prebiotic intake period),
[4]Effect of stopping FOS supplementation = Mean change between the end of prebiotic supplementation and the end of the study (3 weeks follow-up period),
[5]One sample t-test on mean differences.

Phagocytic activity of granulocytes and monocytes were significantly decreased by the ingestion of FOS: Phagocytic activity expressed as median fluorescent intensity changed for granulocytes from 130±10 to 52±2 (p<0.001) and for monocytes from 75±5 to 26±2 (p<0.001).

This possible decrease in inflammatory process is also suggested by the significant decrease in Interleukin-6 mRNA levels in peripheral blood mononuclear cells after ingestion of FOS (FIG. 3).

Vitamin $B_{12}$ and Folate Status

Neither vitamin $B_{12}$ nor folate serum levels were influenced by the supplementation in FOS: Serum vitamin $B_{12}$ were at 271±143 ng/L before supplementation and at 289±160 ng/L during supplementation. Three subjects, however, were deficient in vitamin $B_{12}$. Two subjects returned to normal status during the study while the other remained deficient throughout study. Serum folate levels were at 5.9±2.0 ug/L before supplementation and at 5.7±1.9 ug/L during supplementation.

Our results strongly support the bifidogenic effects of fructooligosaccharides in elderly subjects with a 2 log increase in bifidobacteria counts since our frail elderly subjects showed low counts at the beginning of the study. A diminution in inflammatory process is suggested by the decreased expression of IL-6 mRNA in peripheral blood monocytes.

Indeed, the present study confirms the positive effect of FOS supplementation on bifidobacteria observed in adults and elderly (FIG. 2), indicating that elderly respond to prebiotic (FOS) intake by an increase in bifidobacteria like younger adults or even better if the bifidobacteria counts are low. Further 8 g of FOS or less seems to be sufficient to achieve a maximal effect on bifidobacteria counts. While from different studies a dose response seems to be present, single studies indicate that above a threshold of 4-5 g/day a maximal response is obtained and the increase in bifidobacteria seems to be more dependent of the initial number (FIGS. 1 and 2). Often FOS added to the diet increased the levels of bifidobacteria at the expense of potentially harmful bacteria, clostridia and *Bacteroïdes* mainly. But we observed a significant increase in *Bacteroïdes* throughout the study (tables 2a & 2b).

We observed an important decrease in phagocytic activity. This decrease in phagocytic activity could be a reflection of decreased activation of macrophages linked to a possible reduction in pathogenic bacteria, and thus suggesting a diminution in inflammation due to lower endotoxin load. Surprisingly, however, this possible decrease in inflammatory process is suggested by the decrease in Interleukin-6 mRNA levels in peripheral blood mononuclear cells (FIG. 3).

Example 2

Food Supplement

A food supplement was prepared by mixing or blending fructooligosaccharide with inulin in the proportions by weight of about 70% fructooligosaccharide to about 30% inulin. The resulting prebiotic mixture may be added or blended with any suitable carrier, for example a fermented milk, a yogurt, a fresh cheese, a rennetted milk, a confectionery bar, breakfast cereal flakes or bars, a drink, milk powder, soy-based product, non-milk fermented product or a nutritional supplement for clinical nutrition.

Example 3

Dry Pet Food

A feed mixture is made up of about 58% by weight of corn, about 5.5% by weight of corn gluten, about 22% by weight of chicken meal, 2,5% dried chicory, 1% carnitine, salts, vitamins and minerals making up the remainder.

The fed mixture is fed into a preconditioner and moistened. The moistened feed is then fed into an extruder-cooker and gelatinised. The gelatinised matrix leaving the extruder is forced through a die and extruded. The extrudate is cut into pieces suitable for feeding to dogs, dried at about 110° C. for about 20 minutes, and cooled to form pellets.

This dry dog food is particularly intended for decreasing inflammatory process and/or abnormal activation of non specific immune parameters, such as phagocytes.

Example 4

Wet Canned Pet Food

A mixture is prepared from 56% of poultry carcass, pig lungs and pig liver (ground), 13% of fish, 16% of wheat flour, 2% of plasma, 10.8% of water, 2.2% of dyes, 1% of semi refined kappa carrageenan, inorganic salts and 9% oil rich in monounsaturated fatty acids (olive oil) and 3% chicory. This mixture is emulsified at 12° C. and extruded in the form of a pudding which is then cooked at a temperature of 90° C. It is cooled to 30° C. and cut in chunks.

30% of these chunks (having a water content of 58%) is incorporated in a base prepared from 23% of poultry carcass, 1% of guar gum, 1% of dye and aroma and 75% of water. Tinplate cans are then filled and sterilized at 127° C. for 60 min.

The invention claimed is:

1. A method of decreasing inflammation caused by phagocyte activity in an elderly mammal comprising administering a nutritional composition comprising an effective amount of a prebiotic comprising fructooligosaccharide to the elderly mammal having a pre-existing inflammation caused by phagocyte activity, the prebiotic being administered to the elderly mammal in an amount between 4 to 8 g/day.

2. A method according to claim 1, which comprises administering an effective amount of a probiotic to the elderly mammal.

3. A method according to claim 2 wherein the probiotic is selected from the group consisting of Bifidobacterium bifidum, Streptococcus thermophilus and combinations thereof, the probiotic being in a mixture with the prebiotic.

4. A method according to claim 1, wherein the prebiotic comprises inulin.

5. A method according to claim 1 wherein the prebiotic comprises, by weight, about 60% to about 80% fructooligosaccharide and about 20% to about 40% inulin.

6. A method according to claim 1 wherein the prebiotic is in a composition having other components.

7. A method according to claim 1 wherein the nutritional composition decreases the abnormal activation of non-specific immune parameters in the mammal.

8. A method according to claim 1 wherein the nutritional composition is selected from the group consisting of medicament, food, pet food and combinations thereof.

* * * * *

SEQUENCE LISTING

<160> NUMBER OF SEQ ID NOS: 4

<210> SEQ ID NO 1
<211> LENGTH: 30
<212> TYPE: DNA
<213> ORGANISM: Artificial sequence
<220> FEATURE:
<223> OTHER INFORMATION: Synthesized: IL-6 forward primer

<400> SEQUENCE: 1
ctgcaggaac tggatcagga cttttgtact                                30

<210> SEQ ID NO 2
<211> LENGTH: 30
<212> TYPE: DNA
<213> ORGANISM: Artificial sequence
<220> FEATURE:
<223> OTHER INFORMATION: Synthesized: IL-6 reverse primer

<400> SEQUENCE: 2
gccttcggtc cagttgcctt ctccctgggg                                30

<210> SEQ ID NO 3
<211> LENGTH: 29
<212> TYPE: DNA
<213> ORGANISM: Artificial sequence
<220> FEATURE:
<223> OTHER INFORMATION: Synthesized: B-actin forward primer

<400> SEQUENCE: 3
cgtttcccgc tcggccgtgg tggtgaagc                                 29

<210> SEQ ID NO 4
<211> LENGTH: 30
<212> TYPE: DNA
<213> ORGANISM: Artificial sequence
<220> FEATURE:
<223> OTHER INFORMATION: Synthesized: B-actin reverse primer

<400> SEQUENCE: 4
ggcgacgagg cccagagcaa gagaggcatc                                30